United States Patent
Majeed et al.

(10) Patent No.: US 10,898,536 B2
(45) Date of Patent: Jan. 26, 2021

(54) METHOD OF INHIBITING PROPIONIBACTERIUM ACNES

(71) Applicants: Muhammed Majeed, Edison, NJ (US); Kalyanam Nagabhushanam, East Windsor, NJ (US); Mahadeva Nayak, Bangalore (IN); Nagarajan Ananthanarayanan, Bangalore (IN)

(72) Inventors: Muhammed Majeed, Edison, NJ (US); Kalyanam Nagabhushanam, East Windsor, NJ (US); Mahadeva Nayak, Bangalore (IN); Nagarajan Ananthanarayanan, Bangalore (IN)

(73) Assignee: Sami Labs Limited, Bangalore (IN)

( * ) Notice: Subject to any disclaimer, the term of this patent is extended or adjusted under 35 U.S.C. 154(b) by 0 days.

(21) Appl. No.: 16/471,140

(22) PCT Filed: Dec. 22, 2016

(86) PCT No.: PCT/US2016/068158
§ 371 (c)(1),
(2) Date: Jun. 19, 2019

(87) PCT Pub. No.: WO2018/118058
PCT Pub. Date: Jun. 28, 2018

(65) Prior Publication Data
US 2020/0038467 A1    Feb. 6, 2020

(51) Int. Cl.
*A61K 36/60* (2006.01)
*A61P 17/10* (2006.01)
*A61K 31/352* (2006.01)

(52) U.S. Cl.
CPC ............ *A61K 36/60* (2013.01); *A61K 31/352* (2013.01); *A61P 17/10* (2018.01)

(58) Field of Classification Search
None
See application file for complete search history.

(56) References Cited

PUBLICATIONS

Rajkumar A. et al. Biosynthesis of Silver Nanoparticles from A. hirsutus Leaf Extracts . . . Int J of Research in Pharmaceutical and Nano Sciences 4(1)28-39, 2015. (Year: 2015).*
Narayanaswamy R. et al. Cosmetic Potential of Southeast Asian Herbs. Phytochemical Reviews 14:419-428, 2015. (Year: 2015).*
Nayak M. et al. Pharmacognostic Evaluation of Leaf and Stem Wood Extracts of A. hirsutus Lam. Pharmacognosy J 9(6)887-894, 2017. (Year: 2017).*
Dibinlal D. et al. Pharmacognostical Studies on the Bark of A. hirsutus Lam. Hygeia 2(1)22-27, 2010. (Year: 2010).*
Chan, E. et al. Chemistry and Pharmacology of Artocarpin. Sys Rev Pharm 9(1)58-63, 2018. (Year: 2018).*
Thomas A. et al. Review Study on Pharmacological Importance and Traditional Uses of A. hirsutus Lam. Int J of Scientific Research 5(1)601-604 Nov. 2016. (Year: 2016).*
Thomas J. et al. Antimicrobial Activity and Phytochemical Evaluation of Aqueous Extract of A. hirsutus Lam Bark. Global J for Research Analysis 5(6)42-44, Jun. 2016 (Year: 2016).*
Williams et al., (2012) Acne vulgaris, Lancet, 379:361-372.
Venkataraman V. 1972. Wood phenolics in chemotaxonomy of the Moraceae. Phytochemistry. 11:1571-1586.

* cited by examiner

*Primary Examiner* — Ralph J Gitomer

(57) ABSTRACT

The invention discloses the anti-acne potential of α and β pyranocycloartobiloxanthone A and Artonine E, isolated from the stem bark of *Artocarpus hirsutus* by inhibiting the growth of *Propionibacterium acnes*.

3 Claims, 13 Drawing Sheets

α and β pyranocycloartobiloxanthone A    Artonine E    Clindamycin

US 10,898,536 B2

METHOD OF INHIBITING PROPIONIBACTERIUM ACNES

CROSS REFERENCE TO RELATED APPLICATION

This is a national phase application of PCT application no. PCT/US16/68158 filed on 22 Dec. 2016.

FIELD OF THE INVENTION

The invention in general relates to natural molecules of *Artocarpus hirsutus*. More specifically, the invention relates to a method of isolating natural molecules from *Artocarpus hirsutus* and their use in therapeutic management of Acne vulgaris.

BACKGROUND OF THE INVENTION

Description of Prior Art

Acne vulgaris, one of the major diseases of the skin, affects the pilosebaceous unit (hair follicles associated with oil glands). It is caused due to altered follicular keratinisation, hormonal imbalance, immune hypersensitivity, and bacterial (*Propionibacterium acnes* or *P. acnes*) resulting in pustules, nodules, small bumps (papules) and comedones either with blackheads (open) or with whiteheads in the skin (Williams et al., (2012) Acne vulgaris, Lancet, 379:361-372). Many topical and oral medications are being marketed commercially for controlling *P. acnes*, with limited validity owing to their synthetic nature and profound side effects. Pharmaceutical actives possessing remarkable potency; minimal toxicity and capacity to target only the affected sites are in great demand. Therefore, phytochemicals that possess increased safety, tolerability and efficacy against *P. acnes* would be very effective for the treatment of Acne vulgaris. *Artocarpus hirsutus*, belonging to the Moraceae family, is reported to have wide range of therapeutic applications. The bark of the plant is known for treating pimples and skin cracks (*Artocarpus hirsutus*: ENVIS Centre on Conservation of Medicinal Plants, Ministry of Environment, Forest and Climate change, Government of India). This indicates the wound healing and anti-inflammatory potential of *Artocarpus hirsutus* bark. However, the antimicrobial effect of *Artocarpus hirsutus* bark against *Propionibacterium acnes* has never been anticipated or is obvious. The present invention solves this technical problem by disclosing a method for isolating the bioactive molecules from *Artocarpus hirsutus* and evaluating their antimicrobial activity against *P. acnes*.

It is the principle objective of the invention to disclose a method for isolating and identifying the natural molecules present in *Artocarpus hirsutus*.

It is yet another objective of the present invention to disclose the anti-acne potential of the molecules isolated from stem bark of *Artocarpus hirsutus* by inhibiting the growth of *Propionibacterium acnes*.

The present invention fulfils the aforesaid objectives and provides further related advantages.

SUMMARY OF THE INVENTION

The present invention discloses a method for the isolation and characterisation of natural biologically active molecules from stem bark of *Artocarpus hirsutus*. The present invention also discloses the anti-acne potential of isolated molecules of *Artocarpus hirsutus* by their ability to inhibit the growth of *Propionibacterium acnes*.

Other features and advantages of the present invention will become apparent from the following more detailed description, taken in conjunction with the accompanying images, which illustrate, by way of example, the principle of the invention.

DESCRIPTION OF THE MOST PREFERRED EMBODIMENTS

Figure 1:
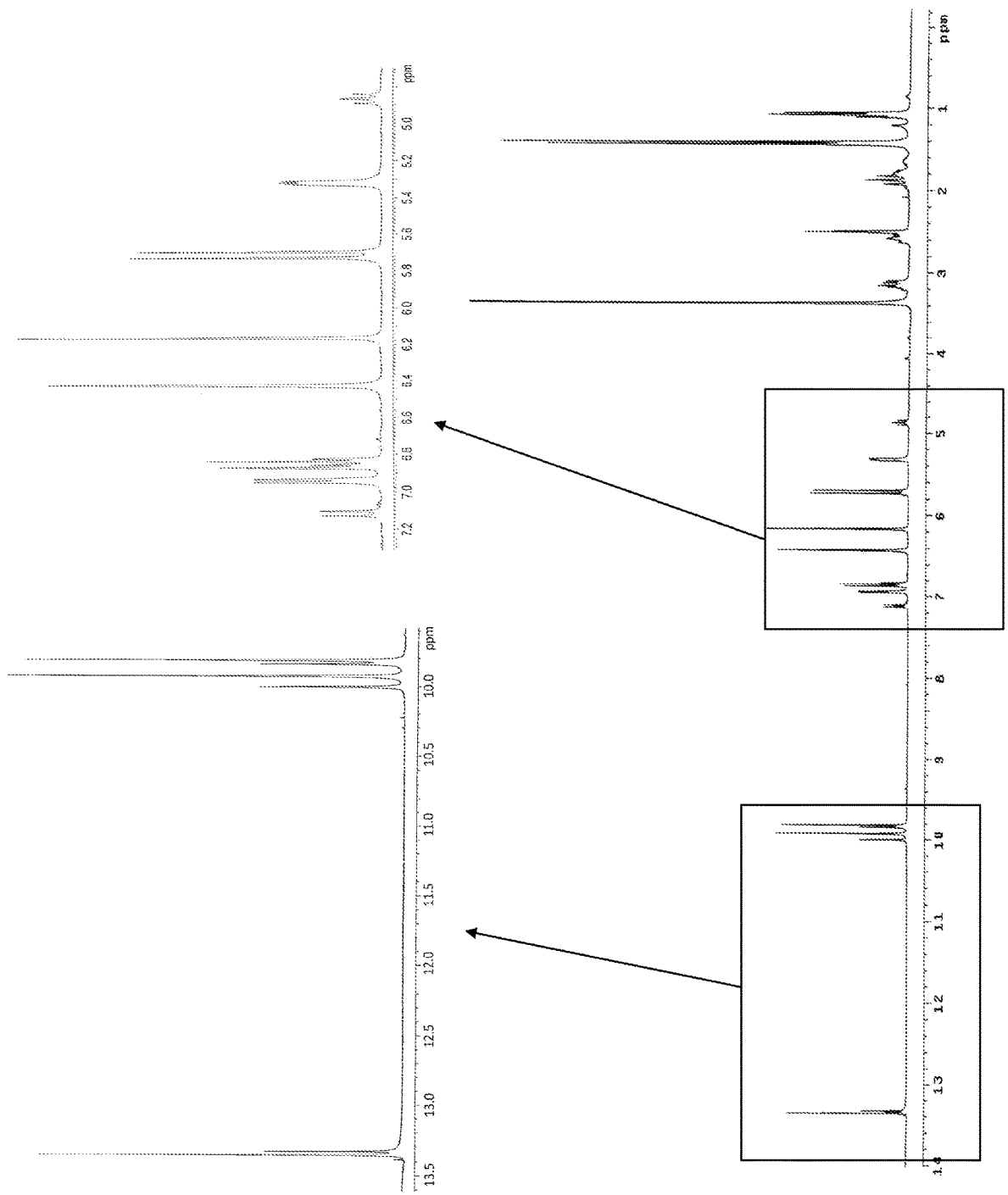
FIG. 1 shows the $^1$H NMR spectra of α and β pyranocycloartobiloxanthone A, isolated from stem bark of *Artocarpus hirsutus*.

In the most preferred embodiment, the present invention discloses a method of isolating natural molecules from the bark of *Artocarpus hirsutus*, said method comprising steps of:
  a) Cutting and drying the stem bark of *Artocarpus hirsutus* and pulverising to coarse powder
  b) Refluxing the stem bark powder of step a with ethanol (w/v ratio 1:10) thrice for 3 hours each to obtain three separate extracts;
  c) Combining the extracts of step b and concentrating at reduced pressure between 55-60° C. and suspending in 2 volumes of water, followed by fractionation with n-hexane (>99% v/v, 2 volumes), chloroform (>99% v/v, 2 volumes), and ethyl acetate (>99% v/v, 2 volumes);
  d) Purifying the chloroform layer of step c on a silica gel column (60-120 mesh) followed by elution with dichloromethane and dichloromethane/Acetone (98:2 to 90:10) and collecting 80 fractions of 250 mL each;
  e) Comparing the fractions of step d using TLC and combining similar fractions (33-67) followed by concentration and drying under vacuum to obtain enriched material;

f) Washing the enriched material obtained in step e with dichloromethane to provide a powder, characterized using spectroscopic techniques as anomeric mixture of α and β Pyranocycloartobiloxanthone A as represented in STR #1, in the ratio of 90-50:10-50 and filtrate;

STR #1

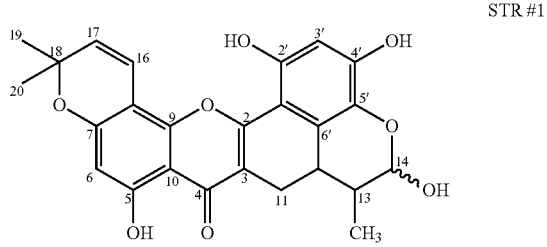 [SMILES: CC1C(O)Oc2c(O)cc(O)c3c2C1Cc1c-3oc2c3c(cc(O)c2c1=O)OC(C)(C)C=C3]

g) Further purification of the filtrate of step f over silica gel and elution with n-hexane-ethyl acetate (70:30) to provide a compound that was characterized using spectroscopic techniques as Artonine E as represented in STR #2.

STR #2

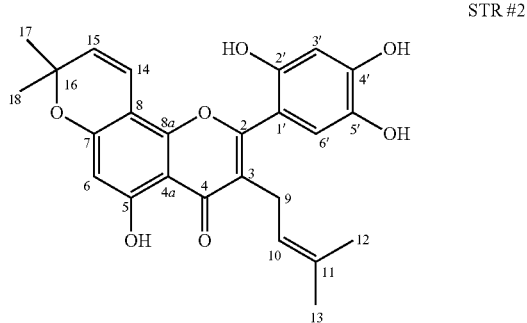 [SMILES: CC(C)=CCc1c(-c2cc(O)c(O)cc2O)oc2c3c(cc(O)c2c1=O)OC(C)(C)C=C3]

In a related embodiment, Pyranocycloartobiloxanthone A is present as α and β anomers in the ratio 70:30.

In a preferred embodiment, the invention discloses a method of inhibiting *Propionibacterium acnes*, said method comprising step of bringing into contact *Propionibacterium acnes* with effective concentration of Pyranocycloartobiloxanthone A, isolated from the stem bark of *Artocarpus hirsutus*. In a related embodiment, Pyranocycloartobiloxanthone A is present as α and β anomers in the ratio 90-50: 10-50 (STR #1). More specifically, Pyranocycloartobiloxanthone A is present as α and β anomers in the ratio 70:30. In yet another preferred embodiment, the invention discloses a method of inhibiting *Propionibacterium acnes*, said method comprising step of bringing into contact *Propionibacterium acnes* with effective concentration of Artonine E, isolated from the stem bark of *Artocarpus hirsutus*.

The specific examples included herein below illustrate the most preferred embodiments of the present invention.

Example I: Isolation of Bioactive Molecules from Stem Bark of *Artocarpus hirsutus*

Collection of Plant Materials

The stem bark of *Artocarpus hirsutus*, was collected from Udupi district, Karnataka, India. All samples were authenticated by botanist and sample voucher was kept in herbarium (RD/HAR-AH/11). The stem bark was cut into small pieces and dried under shade. The dried materials were pulverized to coarse powder and stored in air tight containers.

Preparation of Extracts

The stem bark powder (3 kg) of *Artocarpus hirsutus* was refluxed with ethanol (w/v ratio 1:10), three times for three hours each. The extracts were combined and concentrated at reduced pressure at 55-60° C. The ethanolic extract (yield: 138 g) was filtered and dried completely under vacuum before storing in air tight containers.

Analytical Methods

Normal phase TLC was performed on pre-coated silica gel $F_{254}$ plates (Merck Specialties Private Ltd., Mumbai, India) and the products spot were visualized either by UV (UV-254/366 nm) or by iodine vapours. Liquid chromatography mass spectrometry (LC-MS) analysis was carried out on Finnigan LCQ Advantage Max (Thermo, LAM 10234). $^1$H NMR (300 MHz) and $^{13}$C NMR (75 MHz) spectra were recorded on VARIAN NMR spectrometer. Chemical shifts (δ values) are reported in ppm (parts per million) with respect to TMS as internal standard, DMSO-$d_6$ was used as solvent. Column chromatography was performed over silica gel (mesh 60-120). Infra red spectra were recorded on Perkin Elmer FTIR Spectrometer.

Isolation of Active Molecules

The ethanol extract was suspended in water and fractionated with hexane, chloroform and ethyl acetate. The chloroform extract was further purified on silica gel column chromatography. The column was loaded with silica gel (60-120 mesh) in dichloromethane ($CH_2Cl_2$), eluted with $CH_2Cl_2$ and $CH_2Cl_2$/Acetone and collected 80 fractions of 250 mL each. Similar fractions were combined after verifying the TLC analysis. Fractions 33 to 67 were combined, concentrated and dried under vacuum. The material obtained was washed with $CH_2Cl_2$ to provide Pyranocycloartobiloxanthone A as yellow powder (STR #1). The filtrate was further chromatographed over silica gel and elution with hexane-ethyl acetate (70:30) afforded Artonine E (STR #2) as yellow solid.

Figure 2:
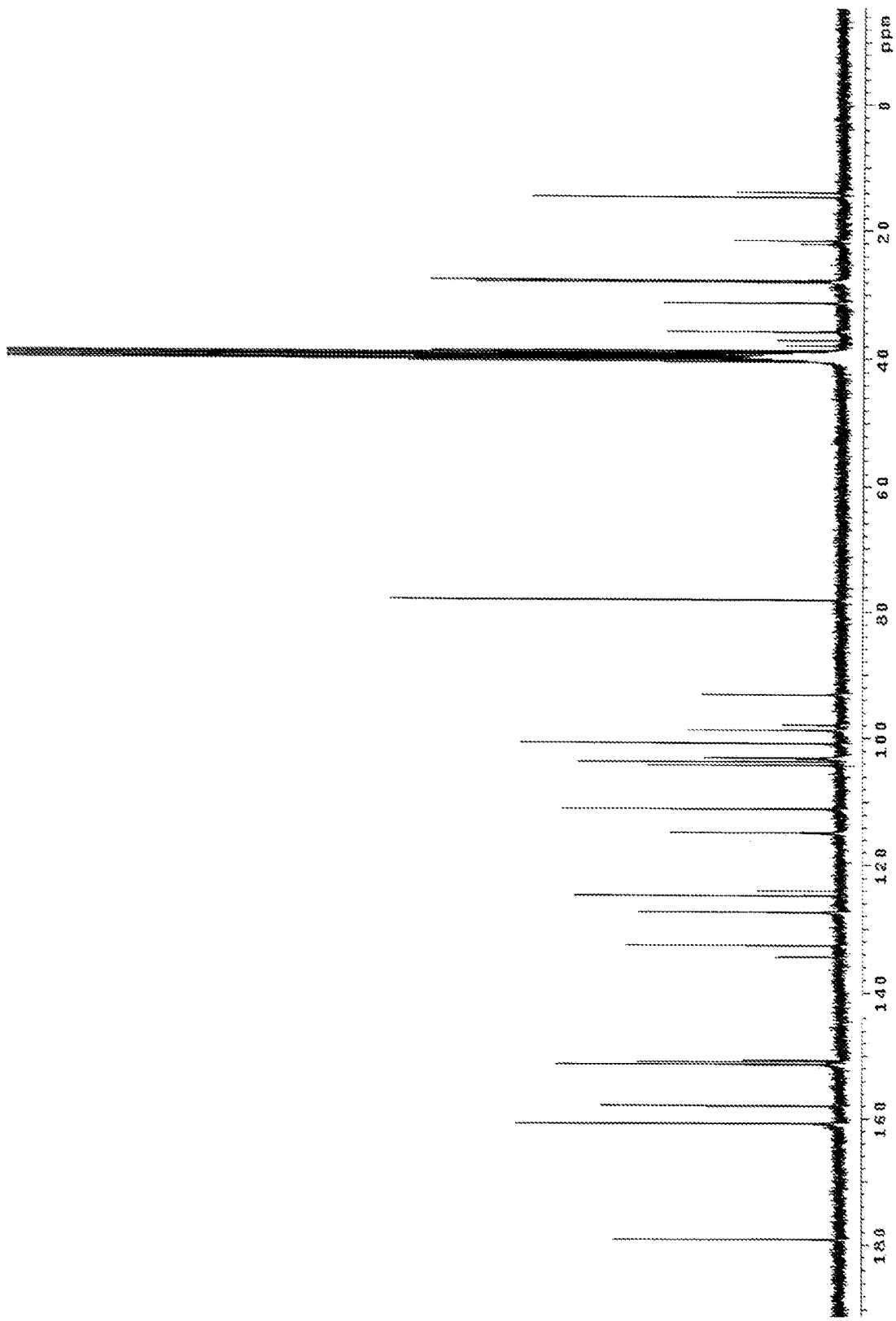
FIGS. 2, 2a and 2b show the $^{13}$C NMR spectra of α and β pyranocycloartobiloxanthone A, isolated from stem bark of *Artocarpus hirsutus*.
Figure 2A:
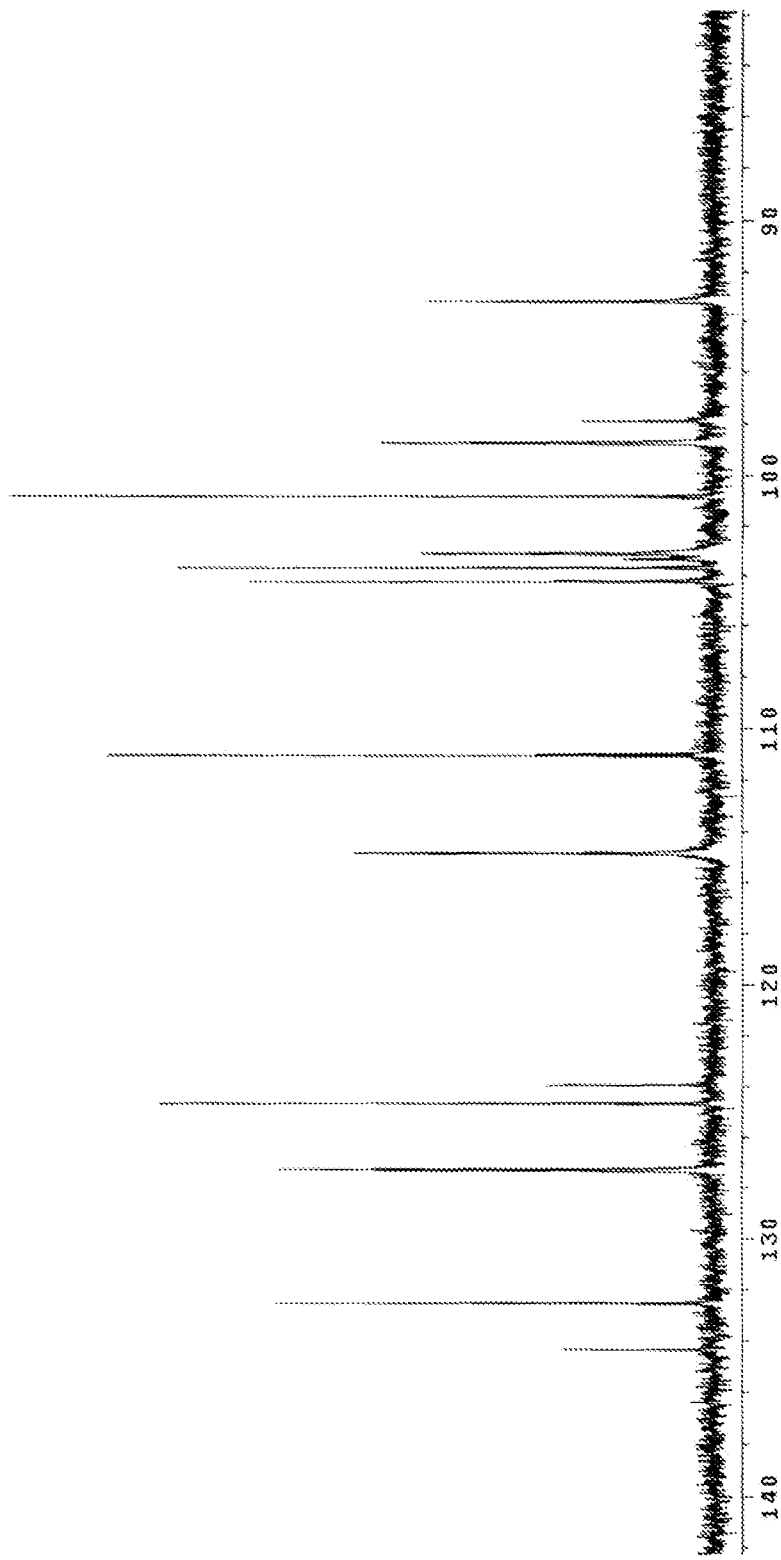
Figure 2B:
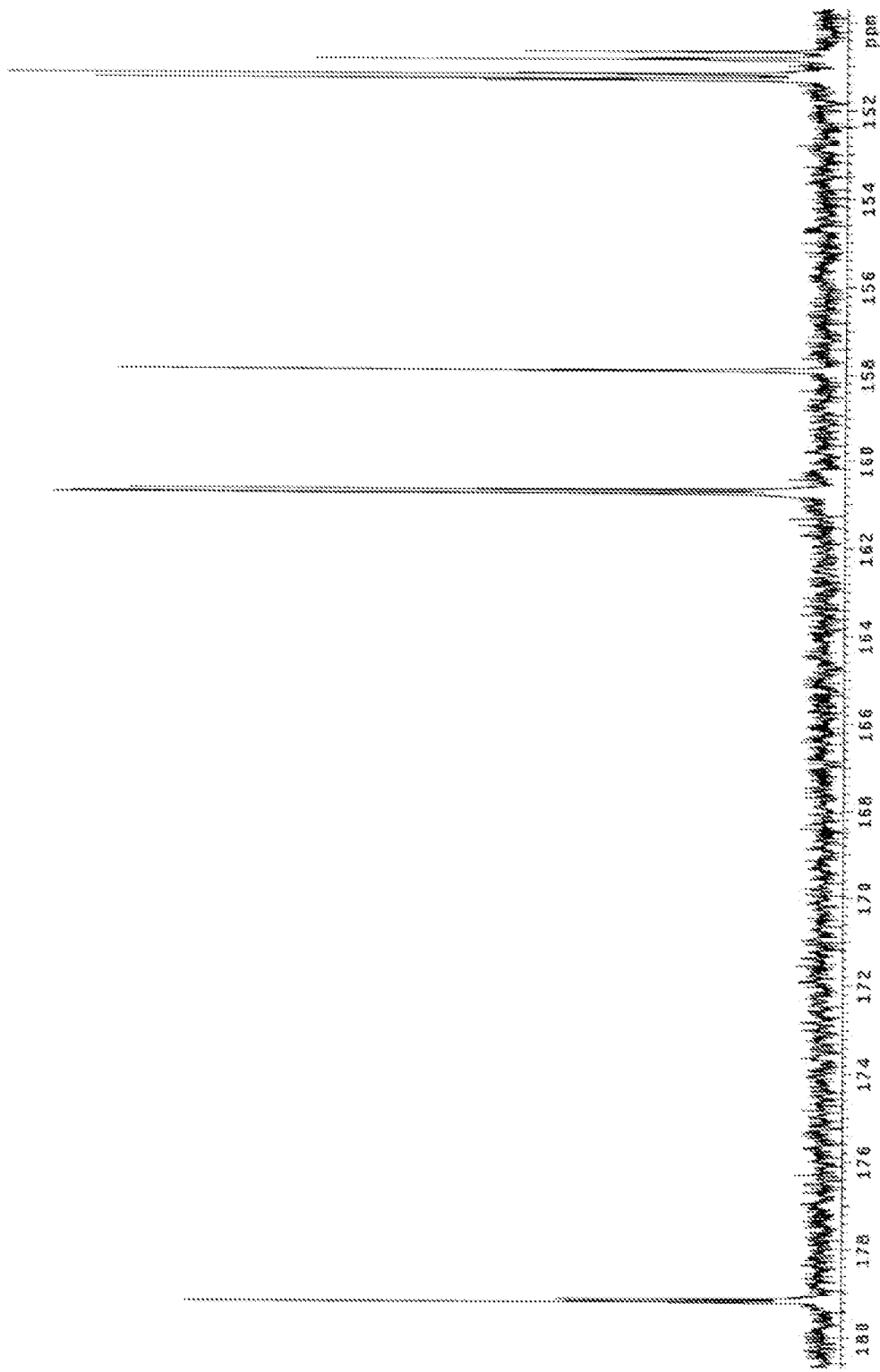

Extensive fractionation and purification of the ethanolic extract of *Artocarpus hirsutus* stem bark on silica gel lead to the isolation of two compounds, characterized as i) a xanthone derivative, Pyrancycloartobiloxanthone A (STR #1) and a flavonoid, Artonine E (STR #2). Pyranocycloartobiloxanthone A was obtained as yellow powder with the melting point 268-270° C. (dec.). The $^1$H (FIG. 1) and $^{13}$C NMR spectra (FIGS. 2, 2a and 2b) of pyranocycloartobiloxanthone A clearly demonstrate the occurrence of two isomers in the ratio of 70 and 30 and were assigned as two anomeric conformers, α (70%) and β (30%) constituted owing to the presence of carbohydrate moiety in the molecule. In consequences, other signals in $^1$H (FIG. 1) and $^{13}$C NMR (FIGS. 2, 2a and 2b) spectra clearly established the ratio of the anomers to be 70:30.

The APCI-MS (FIGS. 3 and 3a) of the pyranocycloartobiloxanthone A corresponds to the molecular ion peak in positive mode at m/z 451.20 (M+H)$^+$ and in negative mode at m/z 449.09 (M−H)$^−$ representing the molecular mass of the molecule with 450. The FTIR spectrum (FIG. 4, Table 1) showed the presence of hydroxyl and conjugated carbonyl moieties with absorption at 3387 and 1659 cm$^{−1}$, respectively.

TABLE 1

FTIR values for pyranocycloartobiloxanthone A
List of Peak area/height

| Peak No. | X(cm−1) | Y (% T) |
|---|---|---|
| 1 | 3280.50 | 92.04 |
| 2 | 1659.32 | 88.49 |
| 3 | 1601.71 | 89.38 |
| 4 | 1548.85 | 78.42 |
| 5 | 1481.99 | 73.64 |
| 6 | 1361.64 | 84.01 |
| 7 | 1336.70 | 85.19 |
| 8 | 1320.99 | 85.00 |
| 9 | 1273.18 | 77.84 |
| 10 | 1228.39 | 88.51 |
| 11 | 1162.21 | 84.41 |
| 12 | 1114.23 | 86.93 |
| 13 | 1085.20 | 88.56 |
| 14 | 1061.45 | 90.16 |
| 15 | 1032.17 | 88.66 |
| 16 | 987.50 | 88.88 |
| 17 | 966.93 | 85.70 |
| 18 | 834.18 | 84.95 |
| 19 | 803.05 | 88.92 |
| 20 | 782.94 | 90.60 |
| 21 | 759.87 | 90.95 |
| 22 | 731.53 | 91.54 |
| 23 | 712.43 | 91.60 |
| 24 | 666.65 | 91.61 |
| 25 | 614.41 | 89.94 |

Figure 3:
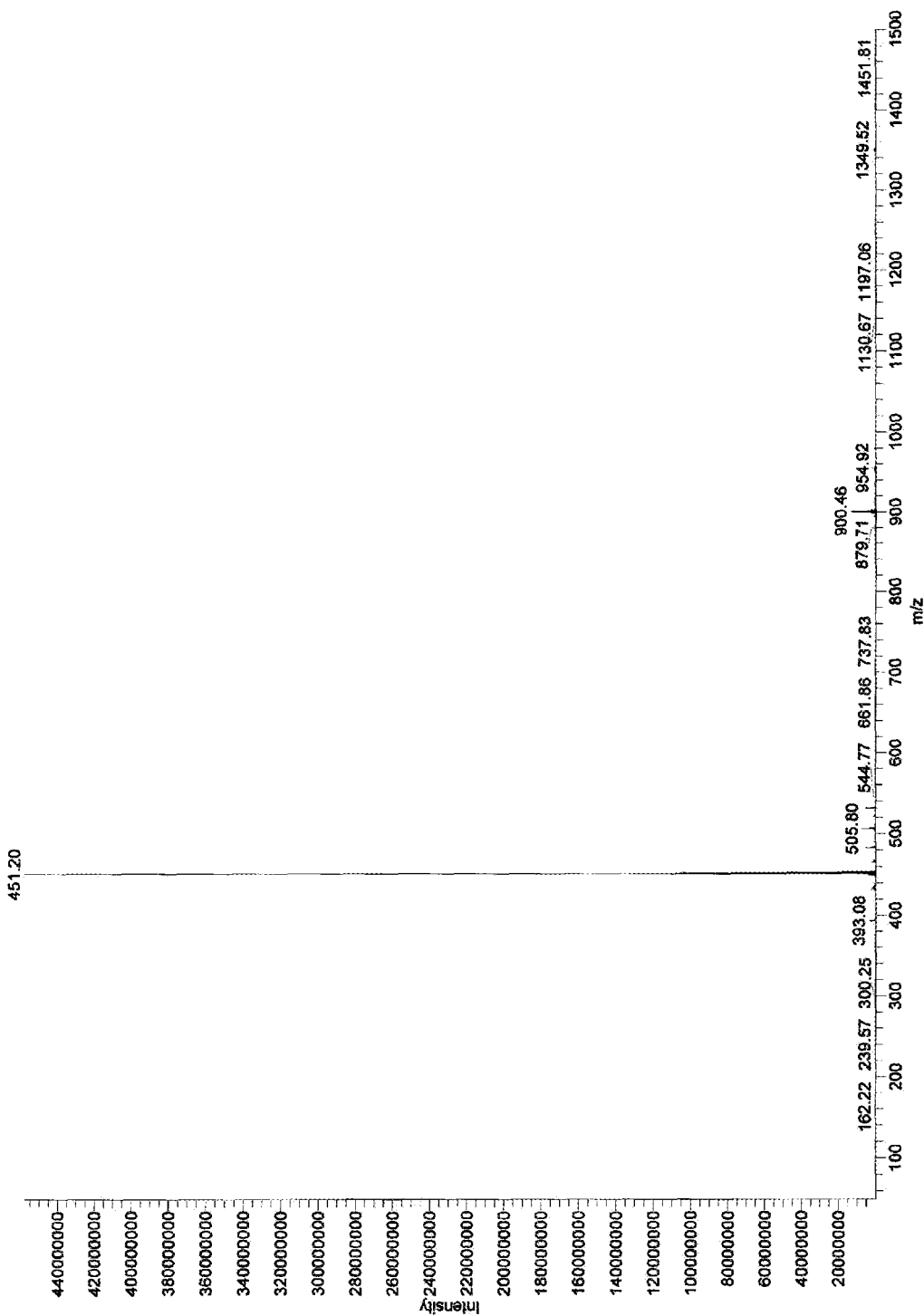
FIGS. 3 and 3a show the Atmospheric pressure chemical ionization-Mass Spectrometer (APCI-MS) data of α and β pyranocycloartobiloxanthone A, isolated from stem bark of *Artocarpus hirsutus*.
Figure 3A:
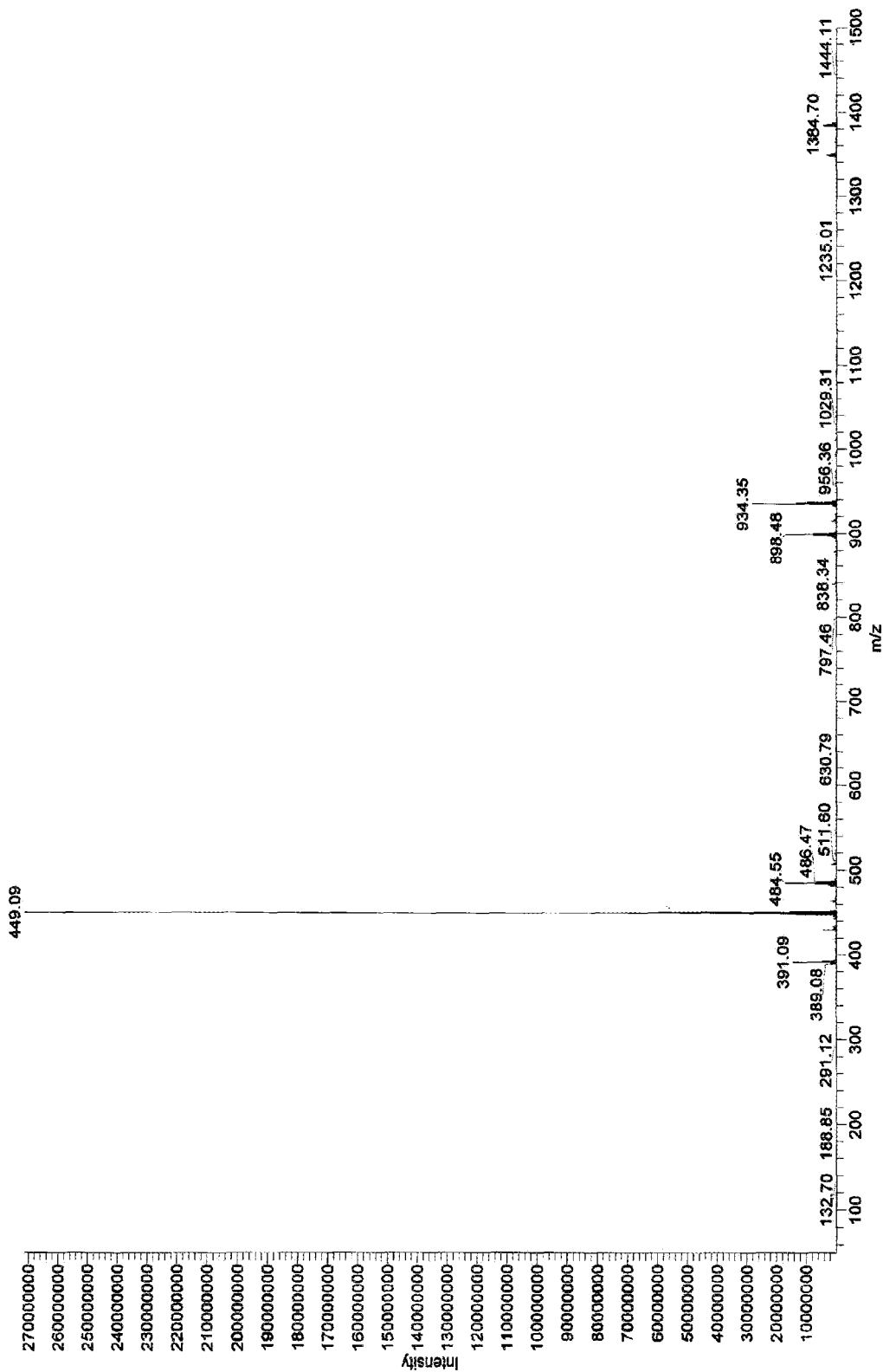
Figure 4:
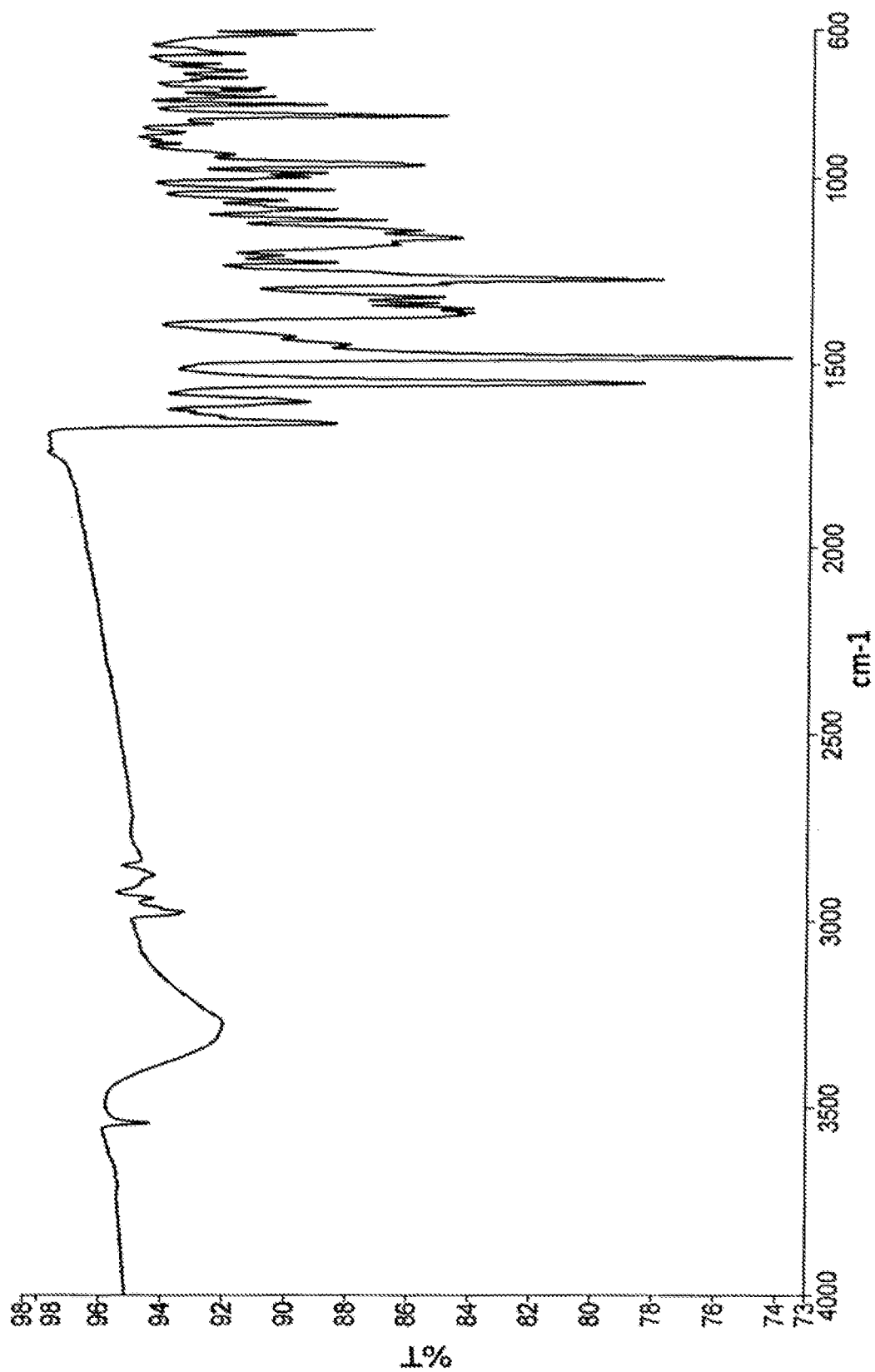
FIG. 4 shows the Fourier transform Infra-red (FTIR) spectrum of α and β pyranocycloartobiloxanthone A, isolated from stem bark of *Artocarpus hirsutus*.
Figure 5:
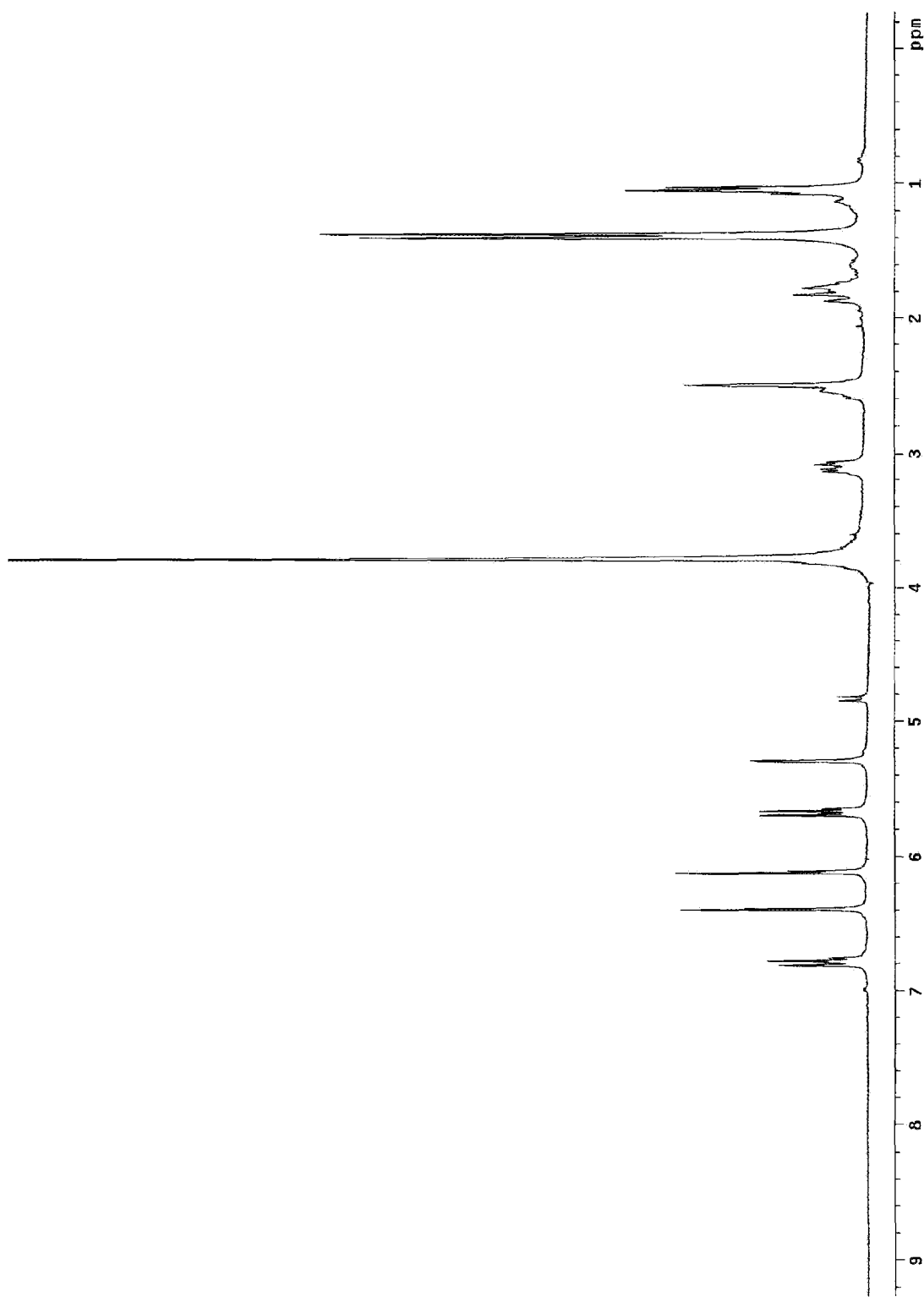
FIG. 5 shows the $D_2O$ exchanged $^1$H NMR spectrum of α and β pyranocycloartobiloxanthone A, isolated from stem bark of *Artocarpus hirsutus*.

The solubility of the compound was relatively poor in most of the solvents except in DMSO and thus $^1$H NMR and $^{13}$C NMR spectra were recorded in DMSO-d6. In $^1$H NMR spectrum, the phenolic OH (5-OH) adjacent to the carbonyl was assigned from the downfield signal at δ 13.36 ppm (70%) and 13.33 ppm (30%) and these two signals appeared due to the presence of the two conformers α and β in about 70:30 ratio. The assignment of two doublets at δ 7.15 ppm (~30%) and 6.94 ppm (~70%) was crucial in $^1$H NMR spectrum. Nonetheless the disappearance of these two signals in D2O exchanged $^1$H NMR spectrum (FIG. 5) ascertained that these two doublet signals are nothing but appeared due to the presence of the hydroxyl group (14-OH) sustaining powerful coupling with anomeric proton (14-H). Thus the signals at δ 7.15 ppm (d, ~30%, β-OH, J=7.5 Hz) and at 6.94 ppm (d, ~70%, α-OH, J=4.2 Hz) were assigned corresponding to the anomeric 14-OH. Similarly, though the anomeric proton (14-H) was expected to appear as a doublet however owing to further coupling with 14-OH, it appeared as two signals one as double doublets at δ 5.32 ppm (dd, ~70%, 14-α-H, J=4.2 Hz, 2.1 Hz) and another one as triplet at 4.87 ppm (t, ~30%, 14-β-H, J=7.8 Hz). The coupling interferences in 14-α/β-H due to 14-OH was disappeared in D2O exchanged $^1$H NMR spectrum (FIG. 5) and signals were clearly appeared as doublets at δ 5.28 (d, ~70%, 14-α-H, J=1.2 Hz) and 4.81 ppm (d, ~30%, 14-β-H, J=8.7 Hz). As expected the signals ratio ~70:30 were reflected in the $^{13}$C NMR spectrum also. It was observed that carbonyl (C-4) peak appeared at δ 179.2 (~70%) and 179.2 (~30%) ppm. Most importantly characteristic anomeric C-14 signal was noticed in two positions at δ 97.6 (~30%) and at 93.2 (~70%) ppm which correspond to C-14β and C-14α anomer respectively. The presence of other characteristic signals both in $^1$H and $^{13}$C NMR spectra confirms the compound as a mixture of α and β-pyranocycloartobiloxanthone A in approximately 70:30 ratio (Table 2). The analytical data of pyranocycloartobiloxanthone A was comparable with that of pyranocycloartobiloxanthone A reported by Hasima et al., (2010), Two new xanthones from *Artocarpus obtusus*, J Asian Nat Prod Res, 12 (2):106-112. However, the reported structure was established as single conformer whereas the instant invention reports this molecule as a mixture of two conformers (α and β). Notwithstanding the illustrative ratio of 70:30 for a mixture of α and β-pyranocycloartobiloxanthone A as elucidated herein above, it is obvious to a person of ordinary skill in the art that the ratio may vary depending on the raw material, seasonal and climatic variation and geographical origin of the raw material. Thus all exemplary variations in the ratio between α and β-pyranocycloartobiloxanthone A are envisioned and encompassed in this patent application. The $^1$H NMR and $^{13}$C NMR spectra of α and β-pyranocycloartobiloxantone A is specified in table 2 with following data:

α and β-pyranocycloartobiloxantone A: Yellow powder with melting point: 268-270° C. (dec.); IR (KBr) $v_{max}$. (Table 1) $^1$H NMR (DMSO, d-6, 300 MHz) (Table 2); $^{13}$C NMR (DMSO-d6, 75 MHz) (Table 2); APCI-MS m/z 451.20 (M+H$^+$) and 449.09 (M−H$^−$) ($C_{25}H_{22}O_8$ requires 450.4373) (FIGS. 3 and 3a).

TABLE 2

Spectral data of α and β-pyranocycloartobiloxantone A

Compound 1 in DMSO-d6

| Position | | $^1$H NMR ($δ_H$), 300 MHz | $^{13}$C NMR ($δ_C$), 75 MHz |
|---|---|---|---|
| 1 | | — | — |
| 2 | | — | 160.8 |
| 3 | | — | 100.8 |
| 4 | | — | 179.2 (70%) |
| | | | 179.1 (30%) |
| 5 | | — | 151.31 |
| 6 | | 6.17 (s, 1H) | 98.7 |
| 7 | | — | 160.7 |
| 8 | | — | 104.23 (70%) |
| | | | 104.18 (30%) |
| 9 | | — | 157.9 |
| 10 | | — | 103.7 |
| 11 | | 1.78-1.92 (m, 1H) | 21.6 (70%) |
| | | 3.10-3.20 (m, 1H) | 22.1 (30%) |
| 12 | | 2.51-2.62 (m, 1H) | 31.2 |
| 13 | | 1.78-1.92 (m, 1H) | 35.7 (70%) |
| | | | 37.0 (30%) |
| 14 | α | 5.32 (dd, 1H, J = 4.2 Hz, 1.95 Hz) (70%) | 93.1 (70%) |
| | β | 4.87 (t, 1H, J = 7.8 Hz) (30%) | 97.9 (30%) |
| 15 | | 1.07 (d, 1H, J = 6.9) (70%) | 14.7 |
| | | 1.10 (d, 1H, J = 6.9 Hz) (30%) | 13.9 |
| 16 | | 6.85 (d, 1H, J = 9.9 Hz) (70%) | 114.8 |
| | | 6.84 (d, 1H, J = 9.9 Hz) (30%) | |
| 17 | | 5.72 (d, 1H, J = 10.2 Hz) | 127.3 |
| 18 | | — | 78.0 |
| 19, 20 | | 1.44 (s, 3H), 1.41 (s, 3H) | 27.7, 28.0 |
| 1' | | — | 111.05 (70%) |
| | | | 110.97 (30%) |
| 2' | | — | 151.28 (70%) |
| | | | 151.17 (30%) |
| 3' | | 6.42 (s, 1H) | 103.1 |
| 4' | | — | 150.8 (70%) |
| | | | 150.7 (30%) |
| 5' | | — | 132.6 (70%) |
| | | | 134.3 (30%) |
| 6' | | — | 124.7 (70%) |
| | | | 123.9 (30%) |
| 5-OH | | 13.36 (s, 1H) (70%) | — |
| | | 13.33 (s, 1H) (30%) | |
| 14-OH | α | 6.94 (d, 1H, J = 4.2 Hz) (70%) | — |
| | β | 7.12 (d, 1H, J = 7.5 Hz) (30%) | |
| 2'-OH | | 9.93 (s, 1H) (70%) | — |
| | | 10.00 (s, 1H) (30%) | |
| 4'-OH | | 9.81 (s, 1H) (70%) | — |
| | | 9.84 (s, 1H) (30%) | |

Artonine E (STR #2) was isolated as yellow powder. The mass spectrum (APCI-MS) (FIGS. 6 and 6*a*) showed the molecular ion peak in positive mode at m/z 437.09 (M+H)$^+$ and in negative mode 435.05 (M−H)$^−$ corresponding to the molecular mass of compound 2 as 436. In the $^1$H NMR spectrum (FIG. 7), three singlets at δ 6.68, 6.46 and 6.21 correspond to three aromatic protons of (H-3', H-6' and H6) whereas the signal at δ 13.2 ppm represents the chelated phenolic proton (5-OH). The presence of prenyl side chain was confirmed from its the corresponding characteristic signals at δ 5.05 (t, 1H, J=6.9 Hz, H-10), 3.03 (d, 2H, J=6.9 Hz, H-9), 1.56 (s, 3H, H-13) and 1.41 (s, 3H, H-12). Similarly, signals at δ 6.52 (1H, d, J=9.9 Hz, H-14), δ 5.69 (1H, d, J=9.9 Hz, H-15), δ 1.41 (6H, s, H-17 and H-18) ascertained the presence of 2,3-dimethylpyran ring. The presence of characteristic signals in $^{13}$C NMR spectrum (FIG. 8) also confirms the structure. It was noticed that the analytical values were correlated well with Sritularak et al, (2010) New 2-Arylbenzofurans from the Root Bark of *Artocarpus lakoocha*, Molecules, 15:6548-6558, and consequently was identified as Artonine E with the following spectral data.

Figure 6:
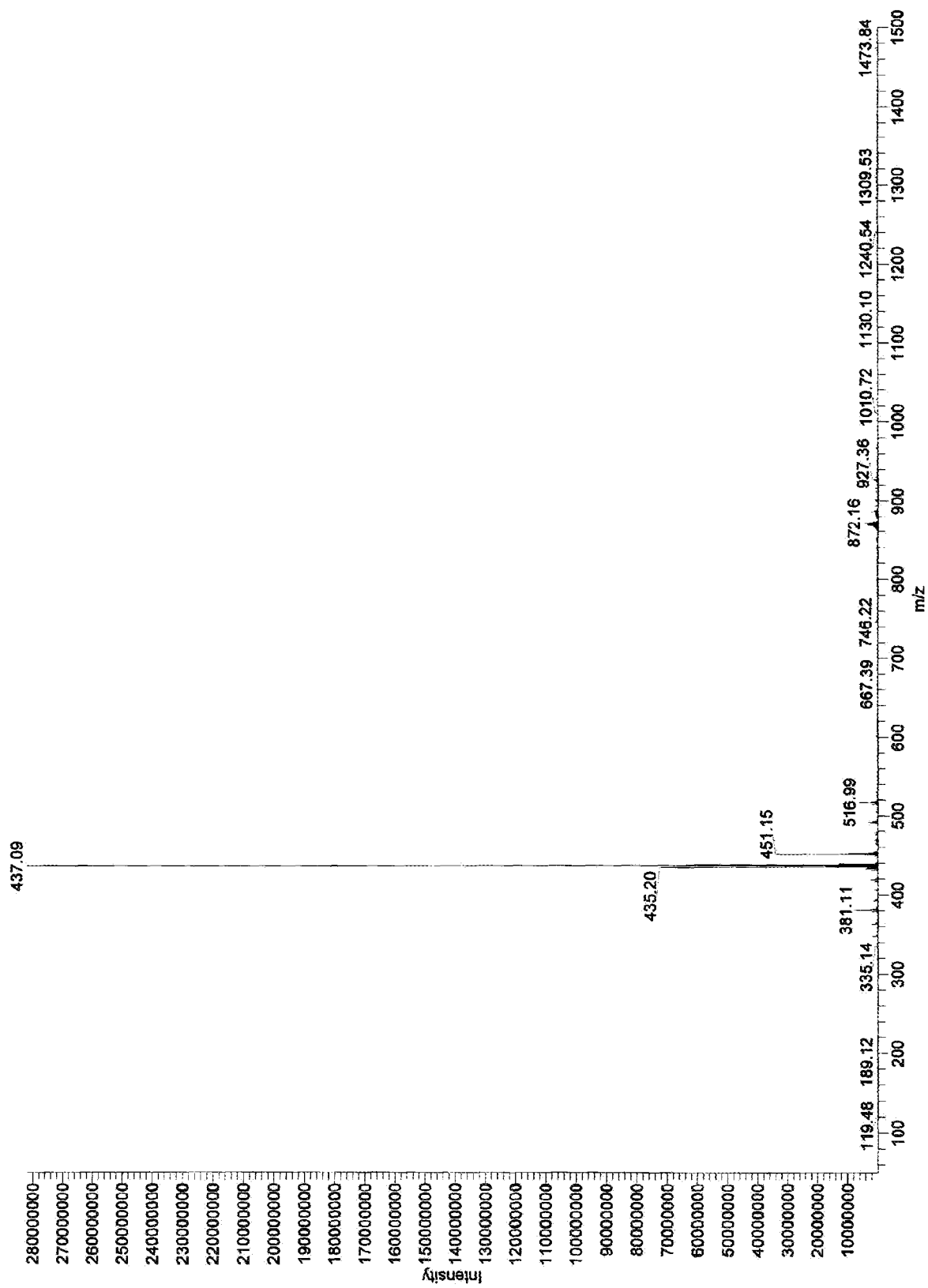
FIGS. 6 and 6a show the Atmospheric pressure chemical ionization-Mass Spectrometer (APCI-MS) data of Artonine E, isolated from stem bark of *Artocarpus hirsutus*.
Figure 6A:
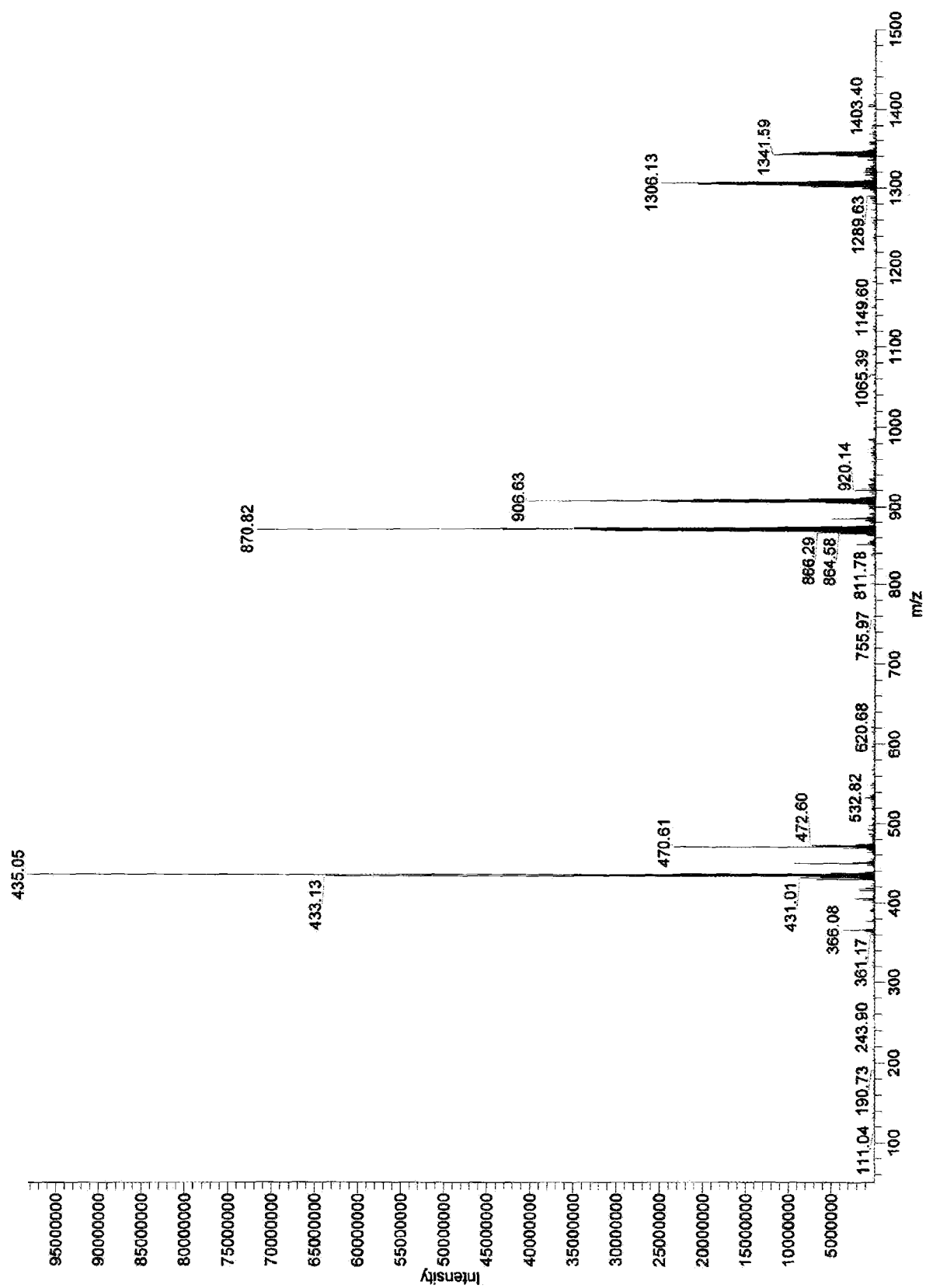
Figure 7:
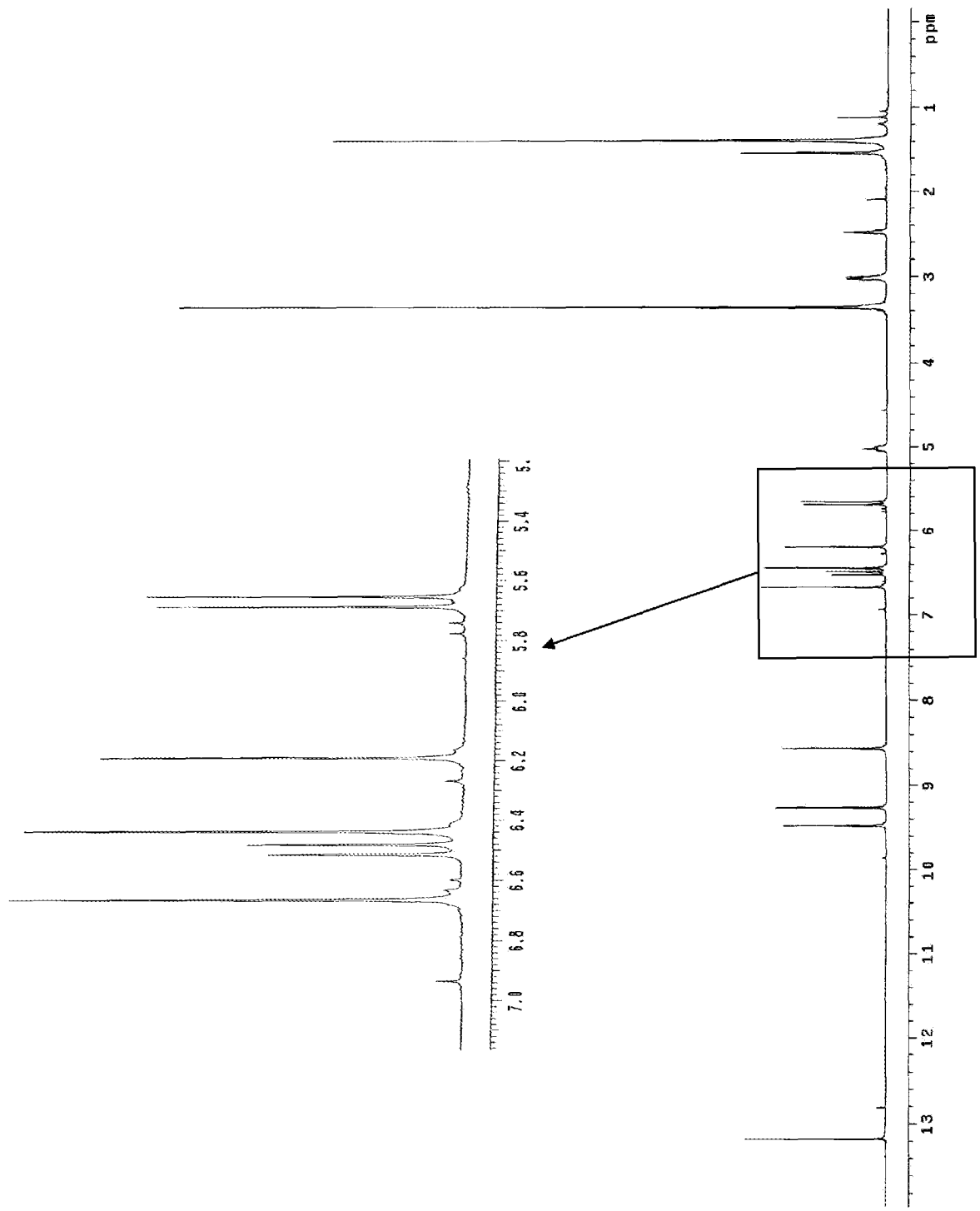
FIG. 7 shows the $^1$H NMR spectra of Artonine E, isolated from stem bark of *Artocarpus hirsutus*.
Figure 8:
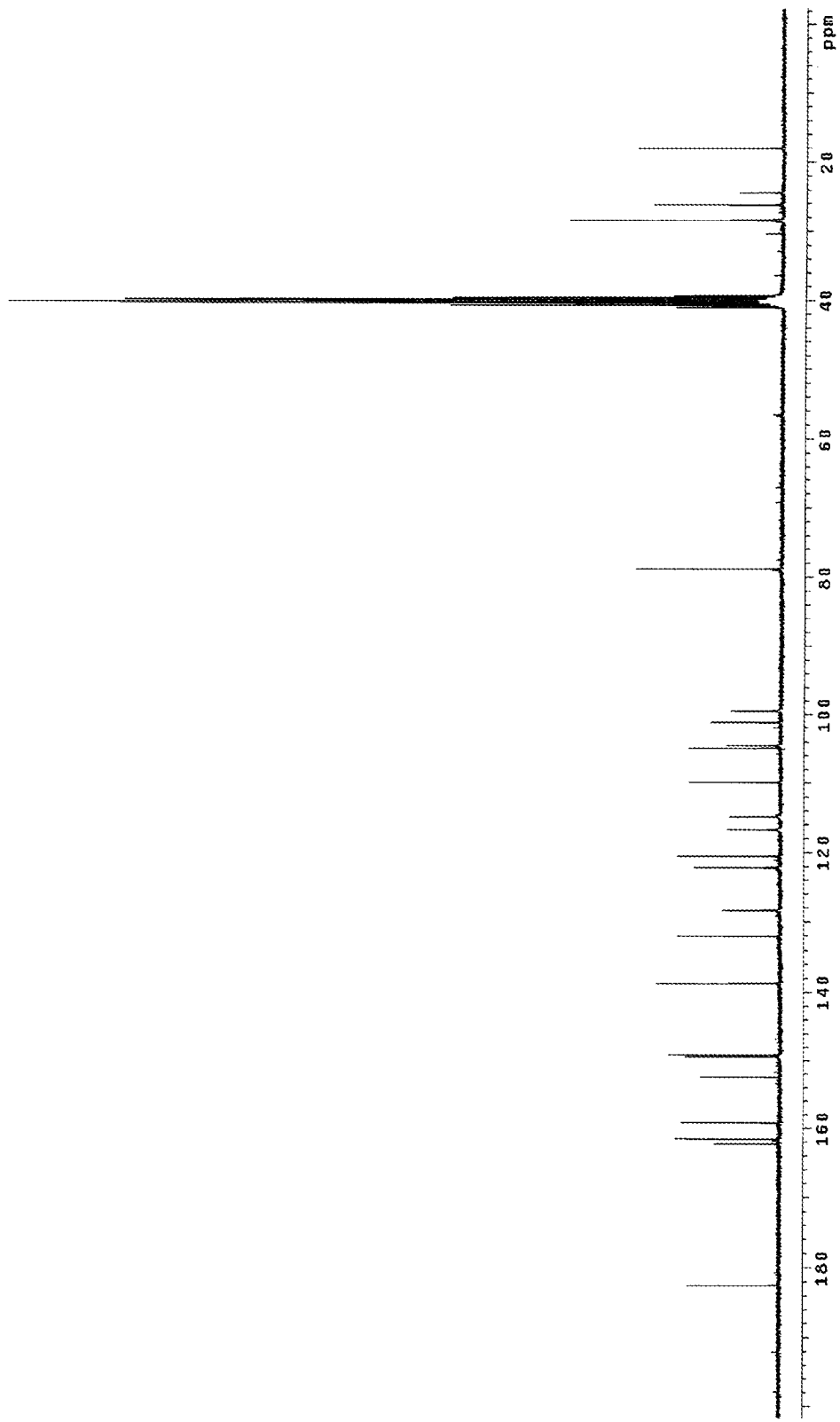
FIG. 8 shows the $^{13}$C NMR spectra of Artonine E, isolated from stem bark of *Artocarpus hirsutus*.

Artonine E: Yellow powder with melting point: 242-246° C.; IR (KBr) $v_{max}$ 3426, 2982, 1642, 1560, 1523, 1462, 1355, 1154, 828, 767, 698 cm$^{-1}$. UV (Methanol) max 204, 267.5, 350 nm. $^1$H NMR (DMSO-d6, 300 MHz): δ 13.2 (s, 1H, 5-OH), 9.5, 9.3, 8.6 (3s, 3H, 2',4', 5'-OH), 6.68 (s, 1H, H-6'), 6.52 (d, 1H, J=9.9 Hz, H-14), 6.46 (s, 1H, H-3'), 6.21 (s, 1H, H-6), 5.69 (d, 1H, J=9.9 Hz, H-15), 5.05 (t, 1H, J=6.6 Hz, H-10), 3.03 (d, 2H, J=6.6 Hz, H-9), 1.56 (s, 3H, H-13), 1.41 (s, 9H, H-12, H-17 and H-18) (FIG. 7); $^{13}$C NMR (DMSO-d6, 75 MHz): δ 181.8 (C-4), 161.7 (C-2), 160.9 (C-5), 158.5 (C-7), 151.7 (C-8a), 148.8 (C-2'), 148.5 (C-4'), 138.0 (C-5'), 131.4 (C-11), 127.7 (C-15), 121.5 (C-10), 119.9 (C-3), 116.1 (C-6'), 114.2 (C-14), 109.3 (C-1'), 104.2 (C-4a), 103.9 (C-3'), 100.5 (C-8), 98.8 (C-6), 78.1 (C-16), 29.6 (C-17), 27.7 (C-18), 25.5 (C-13), 23.7 (C-9), 17.4 (C-12) (FIG. 8); APCI-MS m/z 437.09 (M+H$^+$) and 435.05 (M−H$^−$), (C$_{25}$H$_{24}$O$_7$ requires 436.4539) (FIGS. 6 and 6*a*).

Example II: Antiacne Potential of Pyranocycloartobiloxantone A and Artonine E

In vitro anti-acne activity of isolated compounds 1 and 2 from the stem bark extract of *Artocarpus hirsutus* were evaluated against acne causing bacterium, *Propionibacterium acnes*. The antibacterial activity was determined by agar well diffusion method. The minimum inhibitory concentration (MIC) of the compounds were then ascertained by broth micro dilution method.

Microorganisms: Acne causing bacterium *Propionibacterium acnes* (ATCC 11827) was procured from American type culture collection Rockville, USA.

Media: Reinforced Clostridial Agar (Hi Media; M154) and Reinforced Clostridial broth (Hi Media; M443) were used in the experiments.

Determination of Antibacterial Activity

The antibacterial activities of isolated compounds were performed by agar well diffusion method. The samples were dissolved in DMSO to obtain a concentration in the range of 0.5-100 mg/mL. *Propionibacterium acnes* was cultured on Reinforced Clostridial Agar (RCA) M154 procured from Hi Media and incubated at 37° C. for 48 h in an anaerobic chamber providing gas mixture containing 80% nitrogen, 10% carbon dioxide and 10% hydrogen. The bacterial culture was suspended in sterile normal saline and adjusted to 1.0×10$^8$ CFU/mL (CLSI, M02-A11; Vol. 32 No. 1). The sterile RCA was seeded with the standardized culture of *P. acnes* and poured into plates. The agar medium was allowed to solidify. Wells of 7 mm diameter equidistant from each other were punched into the agar surface using a sterile borer. Aliquot of each sample, diluent control (DMSO), and Clindamycin as standard antibiotic were loaded in the wells. The plates were kept at 4-8° C. for 3 h and then incubated in the anaerobic chamber for 48 h. The diameter of zone of inhibition around the wells were measured and recorded.

Figure 9:
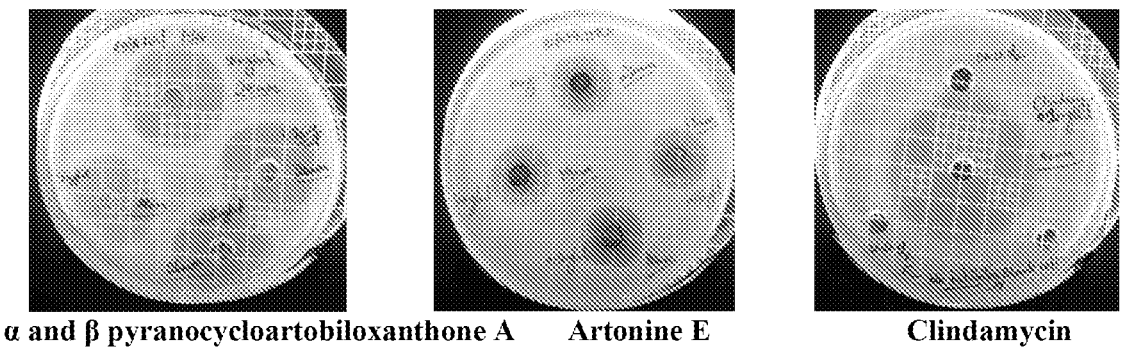
FIG. 9 shows the zone of inhibition of isolated compounds α and β pyranocycloartobiloxanthone A and Artonine E against *P. acnes*. A reference standard (Clindamycin) is included as control.
Figure 10:
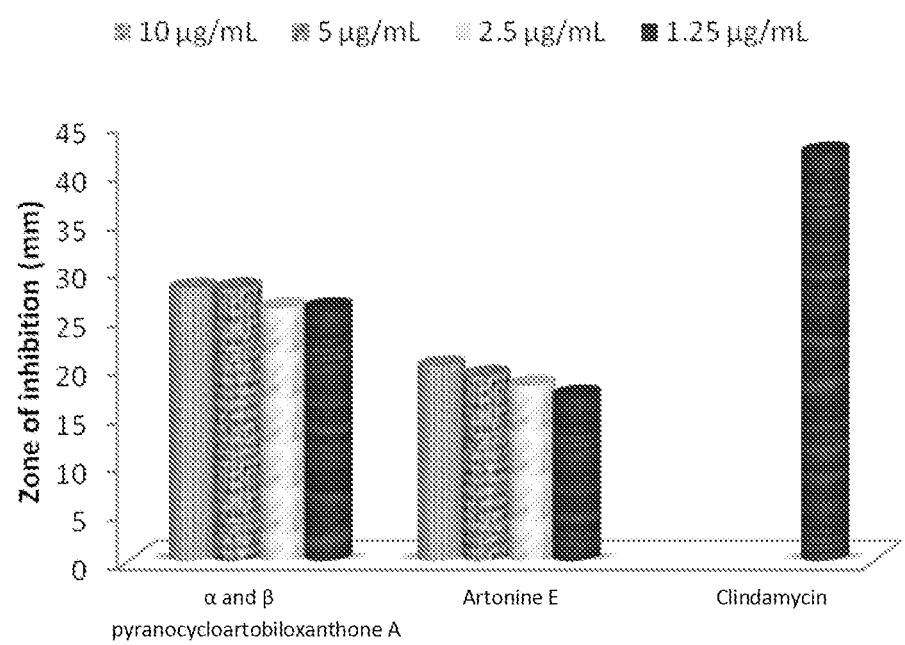
FIG. 10 shows the Graphical representation of the zone of inhibition of compound α and β pyranocycloartobiloxanthone A and Artonine E against *P. acnes*. A reference standard (Clindamycin) is included as control.

The zone of inhibition of isolated compounds: pyranocycloartobiloxantone A and Artonine E around the wells displayed good inhibition. The inhibition was detected in all tested concentrations (10-1.25 µg/mL) (FIG. 9 and FIG. 10).

Determination of Minimum Inhibitory Concentration (MIC)

The minimum inhibitory concentrations (MIC) of the isolated compounds against *P. acnes* were determined by broth micro dilution method. Two-fold dilutions of the isolated compounds were prepared in Reinforced Clostridial broth (RCB) to obtain concentrations in the range of 0.1-2000 µg/mL. The diluted samples were loaded in 96-well micro titre plates. The samples were inoculated with the test culture of *P. acnes* so that the final concentration of the bacteria in each well is 1×10$^5$ CFU (CLSI, M11-A8; Vol. 32 No. 5). The plates were incubated under anaerobic conditions at 37° C. for 48 h and thereafter observed for inhibition of bacterial growth. The minimum concentration required for inhibiting the growth of *P. acnes* was considered as minimum inhibitory concentration (MIC).

It was observed that the isolated compounds exhibited highly potent anti-acne activity against *P. acnes* with MIC values 2 µg/mL each (Table 3).

TABLE 3

MIC of pyranocycloartobiloxantone A and Artonine E against *P. acnes*

| Sl. No. | Compound | MIC (µg/mL) |
|---|---|---|
| 1 | pyranocycloartobiloxanthone A (α & β) | 2 |
| 2 | Artonine E | 2 |
| 3 | Clindamycin | 0.03 |

To summarise, fractionation of ethanolic extract from the stem bark of *A. hirsutus* yielded a mixture of a xanthone derivative, Pyranocycloartobiloxanthone A constituting α and β conformers in almost 70:30 ratio. The conformers were confirmed from its spectral analysis and reported for the first time. Artonine E was the second molecule isolated from the stem bark and both the compounds exhibited significant anti-acne activity with MIC value of 2 µg/mL each and comparable with antibiotic Clindamycin (MIC=0.03 µg/mL).

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of inhibiting *Propionibacterium acnes*, said method comprising step of bringing into contact *Propionibacterium acnes* with effective concentration of Pyranocycloartobiloxanthone A as represented in STR #1 or Artonine E as represented in STR #2, isolated from the stem bark of *Artocarpus hirsutus*.

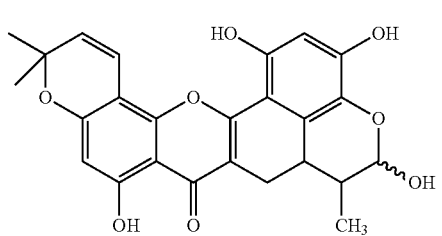
STR #1
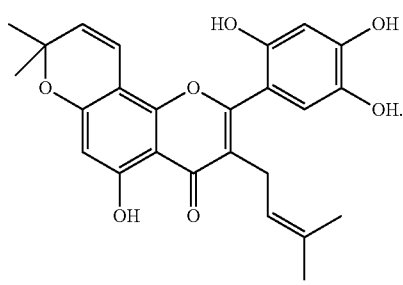
STR #2
2. The method as in claim 1, wherein Pyranocycloartobiloxanthone A is present as α and β anomers in the ratio 90-50:10-50.
3. The method as in claim 2, wherein the ratio of α to β Pyranocycloartobiloxanthone A is 70:30.
* * * * *